United States Patent [19]

Lee et al.

[11] Patent Number: 5,091,571
[45] Date of Patent: Feb. 25, 1992

[54] PROCESS FOR PREPARING N,N'-DISUBSTITUTED UREA

[75] Inventors: Chul Woo Lee, Choongnam; Jae Sung Lee, Kyungbuk; Sang Moo Lee, Choongnam, all of Rep. of Korea

[73] Assignee: Lucky, Ltd., Seoul, Rep. of Korea

[21] Appl. No.: 606,721

[22] Filed: Oct. 31, 1990

[30] Foreign Application Priority Data

Nov. 2, 1989 [KR] Rep. of Korea .................. 89-15880
Dec. 28, 1989 [KR] Rep. of Korea .................. 89-19935

[51] Int. Cl.$^5$ .................. C07C 275/28; C07C 275/30
[52] U.S. Cl. .................................. 564/52; 564/47; 564/48; 564/53; 564/55
[58] Field of Search .............. 564/52, 48, 47, 55, 564/53

[56] References Cited

U.S. PATENT DOCUMENTS

4,052,454 10/1977 Zajacek et al. .................. 564/52
4,603,216 7/1986 Grate et al. .................. 560/24

FOREIGN PATENT DOCUMENTS

0319111 7/1989 European Pat. Off.

OTHER PUBLICATIONS

Oh et al., Ind. Eng. Chem. Res. 1991, 30, 1456-1461.
Fukuoka et al., Chemtech Nov. 198 , 670-676.
Can J. Chem., 40, 1718, 1962.
J. Org. Chem., 37, 2670, 1972.
J. Org. Chem., 26, 3309, 1961, Franz et al.
J. Am. Chem. Soc., 93, 6344, 1971.
J. Org. Chem. vol. 40 (19), 2819, 1975, Dieck et al.

*Primary Examiner*—Richard L. Raymond
*Assistant Examiner*—Shailendra Kumar
*Attorney, Agent, or Firm*—Birch, Stewart, Kolasch & Birch

[57] ABSTRACT

A process for preparing N, N-disubstituted urea and more particularly, to an improved process for preparing N,N'-disubstituted urea derivatives of the following formula (I) comprising

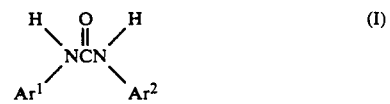

wherein each of Ar$^1$ and Ar$^2$ represents unsubstituted aromatic radical or aromatic radical substituted with halogen, atom, alkyl group, or alkoxy group, and Ar$^1$ and Ar$^2$ are the same or different, reacting aromatic mono-nitro compound, aromatic primary amines, and carbon monoxide in the presence of the catalyst composition consisting of a palladium compound as a main catalyst and an ammonium or a phosphonium salt containing halogen atom aS a co-catalyst, and a non-polar solvent.

8 Claims, 1 Drawing Sheet

PROCESS FOR PREPARING N,N'-DISUBSTITUTED UREA

BACKGROUND OF THE INVENTION

1. Field of the Invention

The present invention relates to a process for preparing N, N-disubstituted urea and more particularly, to an improved process for preparing N,N'-disubstituted urea derivatives of formula (I) comprising

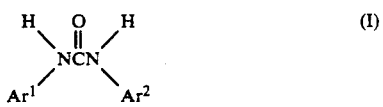

wherein each of $Ar^1$ and $Ar^2$ represents unsubstituted aromatic radical or aromatic radical substituted with halogen atom, alkyl group, or alkoxy group, and $Ar^1$ and $Ar^2$ are the same or different, reacting aromatic mono-nitro compound, aromatic primary amines, and carbon monoxide in the presence of the catalyst composition consisting of a palladium compound as a main catalyst and an ammonium or a phosphonium salt containing halogen atom as a co-catalyst, and a non-polar solvent.

2. Description of the Prior Art

The conventional N,N'-disubstituted urea is an important intermediate for the production of carbamates which are raw materials for agrochemicals. The conventional methods for preparing N,N'-disubstituted urea have heretofore developed by reaction of amines with carbon monoxide in the presence of non-platinum catalysts such as cobalt carbonyl (Can. J. Chem., 40, 1718, 1962), silver acetate (J. Org. Chem., 37, 2670, 1972), and mercuric acetate; sulfur catalyst (J. Org. Chem., 26, 3309, 1961); and selenium catalyst (J. Am. Chem. Soc., 93, 6344, 1971).

Such methods for preparing N,N'-disubstituted urea in the presence of metal compounds except platinum group are not practical since the yield and selectivity of the reaction is quite low. Such methods using compounds such as sulfur catalyst, or selenium catalyst have high yield and selectivity. However, it is very difficult to separate and recover those catalysts. That is, unless the catalysts can be separated for reuse, the catalyst loss generally tends to make the expense of using the process prohibitive for economic purpose.

The processes using palladium group catalysts are disclosed in Japanese Patent Publication No. 53,41,123, Japanese Patent Laid Open Publication Nos. 58-144,363 and 62-59,253, and J. Org. Chem. Vol. 40 (19), 2819, 1975. Among the such disclosures, Japanese Patent Publication No. 53-41,123 and Japanese Patent Laid Open Publication No. 58-144,365 relate to the process for preparing N,N'-disubstituted urea by reaction of amines with carbon monoxide under an elevated temperature and a high pressure. In such methods, it is not only difficult to control the partial pressure of two kinds of gases involved, i.e. carbon monoxide and oxygen, but also there is a danger of explosion due to the oxygen. The method disclosed in J. Org. Chem. Vol. 40 (19), 2819, 1975 results in lower yield. Since tri-n-butyl amine is used together with solvent, the activity of the catalyst is suddenly decreased during the reaction. The process disclosed in Japanese Patent Laid Open Publication No. 62-59,253 gives relatively high yield and selectivity. However, it requires expensive catalysts such as rhodium and ruthenium compounds. Furthermore, the appearance of the resulting N,N'-disubstituted urea is not neat, and the used catalysts are unstable at a high temperature and decomposed around the reaction temperature.

The preparation of N,N'-disubstituted urea using a palladium compound as a catalyst is described in J. Org. Chem., 49 (19), 2819, 1975. Such method comprises the reaction of aromatic mono-nitro compound and aromatic primary amine with carbon monoxide in the presence of a palladium compound, an organic phosphine, tertiary amines, and tetraethyl ammonium chloride. The molar ratio of the aromatic mono-nitro compound to the aromatic primary amine is 1.1:1 to 2:1. Although it is ideal for this reaction to dissolve the palladium compound completely in the aromatic primary amine, it is actually very difficult to achieve. Also the reaction pressure is very low. As a result, the yield of the aromatic urea according to the method is as low as about 64%. Furthermore, when the product solids are separated from the reaction mixture after the reaction, a large amount of the catalyst mixed with the solid product is lost from the reaction mixture. In addition, a part of the palladium compound is decomposed. therefore, it is difficult to recover the catalyst efficiently and almost impossible to re-use the catalyst. Normally, the overall economy of the process depends on the efficiency of the recovery of expensive catalyst such as palladium.

SUMMARY OF THE INVENTION

Accordingly, it is an object of the present invention to provide an improved process for preparing N,N'-disubstituted urea derivatives of the below formula (I) in high yield.

Another object of the present invention is to provide a process of the preparation of N,N'-disubstituted urea which comprises reacting an aromatic mono-nitro compound and aromatic primary amine with carbon monoxide in the presence of a catalyst composition consisting of a palladium compound as a main catalyst and an ammonium or phosphonium salt as a co-catalyst wherein the molar ratio of the aromatic primary amine to the mono-nitro compound in the reaction mixture is more greater than two so as to attain the high yield of the desired product, inhibit the catalyst decomposition during the reaction, and recover the catalyst maintaining the initial activity without any further treatment.

A further object of the present invention is to provide a process of the preparation of N,N'-disubstituted urea derivatives which comprises reacting aromatic primary amine, an aromatic mono-nitro compound, and carbon monoxide in the presence of a catalyst composition wherein the aromatic primary amine is used both as a reactant and as a solvent so as to wash the product solids for the complete recovery of the catalyst and the reaction temperature is 50° to 200° C., preferably 80° to 140° C., and more preferably 100 to 120° C. and the reaction pressure is 5 to 100 atm., preferably 5 to 40 atm.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a process for preparing N, N-disubstituted urea and more particularly, to an improved process for preparing N,N'-disubstituted urea derivatives of the following formula (I) comprising

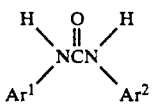
(I)

wherein each of $Ar^1$ and $Ar^2$ represents unsubstituted aromatic radical or aromatic radical substituted with halogen atom, alkyl group, or alkoxy group, and Ar and Arz are the same or different, reacting aromatic mono-nitro compound, aromatic primary amines, and carbon monoxide in the presence of the catalyst composition consisting of a palladium compound as a main catalyst and an ammonium or a phosphonium salt containing halogen atom as a co-catalyst, and a non-polar solvent.

BRIEF DESCRIPTION OF THE DRAWING

The present invention will become more fully understood from the detailed description given hereinbelow and the accompanying drawing which are given by way of illustration only, and thus are not limitative of the present invention, and wherein.

DESCRIPTION OF THE PREFERRED EMBODIMENT

Figure 1:
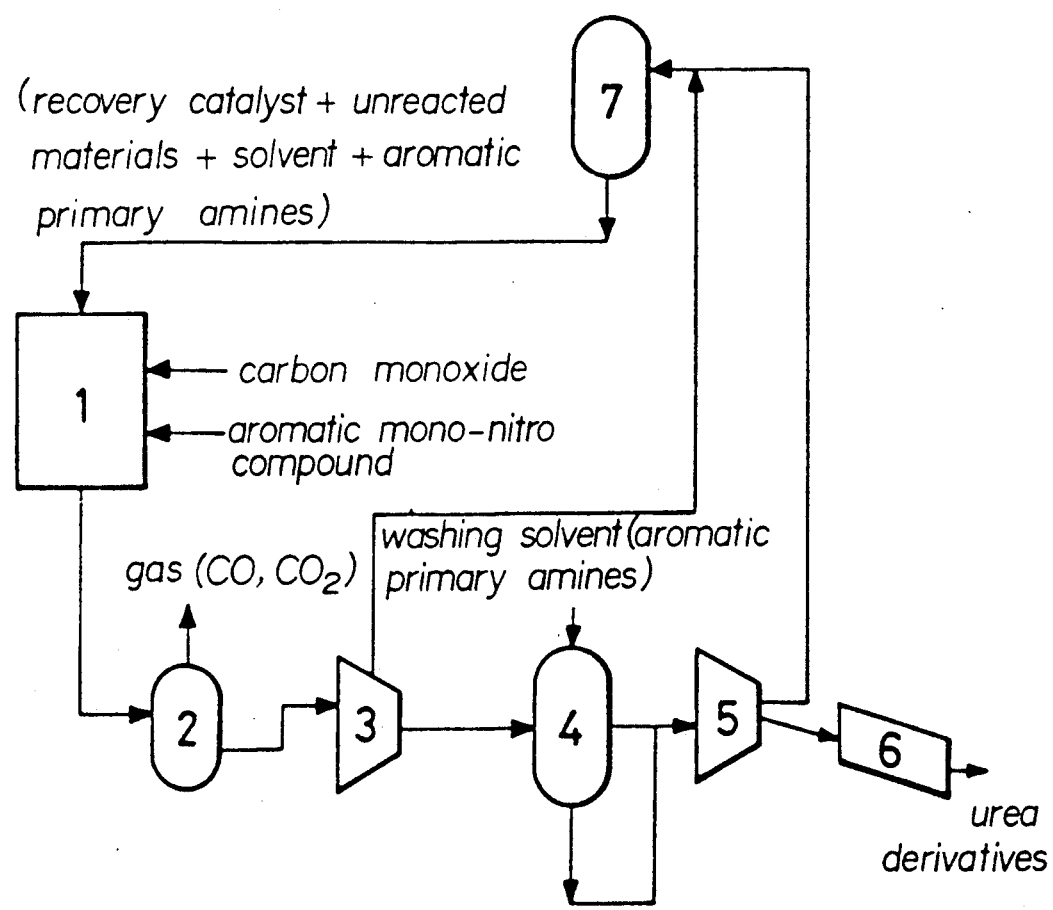
FIG. 1 shows a schematic diagram of the process of the present invention for preparing N,N'-disubstituted urea.

Referring now in detail to the drawings for the purpose of illustrating preferred embodiments of the present invention, the process of the preparation of N,N'-disubstituted urea as shown in FIG. 1 which comprises reacting an aromatic mono-nitro compound, aromatic primary amines, and carbon monoxide in the presence of a catalyst composition consisting of a palladium compound as a main catalyst and an ammonium or phosphonium salt containing halogen atom as a catalyst, and a non-polar solvent.

The aromatic mono-nitro compound is selected from the group consisting of nitrobenzenes, nitronaphthalenes, nitroanthracenes, and nitrobiphenyls. They include, for example, nitrobenzene, o-, m-, or p-nitrotoluene, o-nitro-p-xylene, 2-methyl-1-nitronaphthalene, o-, m- or p-chloronitrobenzene, 1-bromo-4-nitrobenzene, 2-chloro-6-nitrotoluene, 4-chloro-3-nitrotoluene, 1,4-dichloro-2-nitrobenzene, 3,4-dichloro-1-nitrobenzene, alpha-chloro-m-nitrotoluene, and 1,2,4-trichloro-5-nitrobenzene, etc.

The primary aromatic amine is selected from the group consisting of anilines, aminonaphthalenes, aminoanthracenes, and aminobiphenyls. They include aniline, o-, m-, or p-toluidine, o-, m-, p-chloroaniline, alpha- or beta-naphthylamine, 2-methyl-1-aminoaphthalene, and aminotoluene, etc.

Since the primary amine used in the present invention functions not only as a reactant but also as a solvent, it is preferred to use it more than twice greater than two in moles than the mono-nitro compound so that it inhibits the decomposition of the catalyst and makes it easy to recover the catalyst by washing the product solids with the primary amine.

The reaction for the production of N,N'-disubstituted urea represented by the formula (I) proceeds competitively as shown in the following reaction schemes (1) and (2):

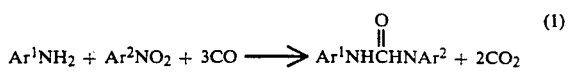

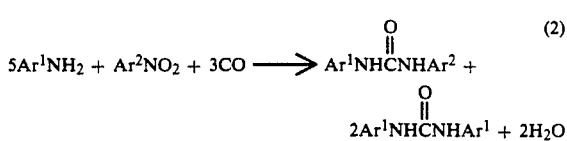

wherein $Ar^1$ and $Ar^2$ are the same as defined above.

The production rate of N,N'-disubstituted urea depends on the molar ratio of the aromatic mono-nitro compound to the aromatic primary amine. As shown in the above equations (1) and (2), when the amount of mono-nitro compound of equations (1) and (2) is same, the larger the amount of aromatic primary amine, the larger the amount of N,N'-disubstituted urea is produced. Because the reaction rate of the equation (2) is increased more rapidly than the reaction rate of the equation (1) when the concentration of the aromatic primary amine increases.

The palladium compounds useful as a main catalyst in the present invention are composed of a divalent palladium ion represented by the following formula (II)

wherein X indicates halogen atom, $NO6hd\ 3$, $OCOCH_3$, and $OCOCF_3$, or represented by the following formula (III)

wherein X is the same as defined above and L indicates $PR_3$ (R is methyl, ethyl, buthyl), phenyl, $C_6H_5NH_2$, and $CH_3CH$, and $ClC_6H_5NH_2$, $CH_3C_6H_4NH_2$ as a ligand. The palladium compounds are, for examples, inorganic salts such as $PdCl_2$, $PdBr_2$, $PdI_2$, $Pd(NO_3)_2$, and $PdSO_4$, and complex compounds such as $PdCl_2(PPh_3)_2$, $Pd(OCOCH_3)_2(PPh_3)_2$, $Pd(OCOCF_3)_2(PPh_3)_2$.

The amount of the main catalyst is preferably 1/10 to 1/3000 mole per mole of the aromatic mono-nitro compound. When the main catalyst of the type $PdX_2$ is used, it is necessary to add the aforementioned ligands of $PR_3$ to the reaction mixture so as to inhibit the deactivation of the catalyst. The amount of the ligand is preferably more than 2 moles per mole of the main catalyst.

The halogen-containing compound used as the co-catalyst is ammonium salts of the formula $[R'rN^+]X^-$ and phosphonium salts of the formula $[R'P^+]X$ wherein R' represents hydrogen atom, paraffinic, aromatic, or paraffinic aromatic group, and X represents halogen atom. Such compound includes, for example, ammonium salts such as tetramethyl ammonium chloride, tetraethyl ammonium chloride, tetrabutyl ammonium chloride, tetramethyl ammonium bromide, tetraethyl ammonium bromide, tetrabutyl ammonium bromide, tetramethyl ammonium iodide, tetraethyl ammonium iodide, tetrabutyl ammonium iodide, trimethyl benzyl ammonium chloride, etc., and phosphonium salts such as tetramethyl phosphonium chloride, tetraethyl phosphonium chloride, tetrabutyl phosphonium chloride, tetramethyl phosphonium bromide, tetraethyl phosphonium bromide, tetrabutyl phosphonium bromide, tetramethyl phosphonium iodide, tetraethyl phosphonium iodide, tetrabutyl phosphonium iodide, etc.

The amount of the co-catalyst is 1 to 20 moles per mole of the main catalyst, i.e. the palladium compound. When the amount of the co-catalyst is less than 1 mole per mole of the main catalyst, the rate of the reaction is negligible. On the other hand, when it is more than 20 moles per mole of the main catalyst, is not economical.

It is preferable to control the amounts of the main catalyst and the ligand so as to dissolve them completely considering the solubilities of each component under the reaction conditions such as a reaction temperature, a reaction pressure, an amount of the aromatic primary amine, and an amount of the solvent.

After the reaction, the main catalyst and the co-catalyst can be easily separated and recovered from the reaction mixture by simple filtration since the product N,N'-disubstituted urea is solid. The aromatic primary amine as a reactant is employed to wash the solid product by recovering the catalyst mixed with the solid product almost completely.

The process of the present invention is carried out in the absence of a solvent, but the use of the solvent is not precluded. Suitable solvents are preferably non-polar solvents such as benzene, toluene, xylene, which hardly dissolve N,N'-disubstituted urea. The reaction temperature is generally held in the range of 50° to 200° C., preferably from 80° to 140° C., and more preferably from 100° to 120° C. When reaction temperature is lower than the above range, a large amount of mononitro compound remains unreacted, whereas, when the reaction temperature is higher than the above range, the catalyst tends to be deactivated or decomposed.

Even though it is possible to carry out the reaction at any pressure greater than 1 atm., the reaction pressure is generally held in the range of 5 to 100 atm., and preferably 5 to 40 atm. When the reaction pressure is less than 5 atm., the reaction rate is too slow. When the reaction pressure is more than 100 atm., it requires much expenses for high pressure equipments.

The reaction time period depends on the nature and amount of reactants, the reaction pressure, the reaction temperature, the type and the amount of catalyst. However, it is generally in the range of 10 minutes to 10 hours. After completion of the reaction, the final product, N,N'-disubstituted urea, is recovered as a solid from the reaction mixture by filtration or centrifugation and washing. Since the main catalyst, co-catalyst, unreacted materials, and solvent present in the remaining liquid phase, the main catalyst and co-catalyst are almost perfectly recovered from the mixture by the filtration of product solids. The obtained urea derivatives are subjected to a conventional procedure including washing and separation under reduced or elevated pressure, centrifugation, thereby obtaining the product with high purity.

The aromatic primary amine is preferably used for washing, and more preferably aromatic primary amine is exactly same as the reactant since it can be used for the next process without any further treatment.

As shown in FIG. 1, raw materials are charged into a reactor 1 and reacted. After the reaction is completed, the gases which are mainly carbon monoxide and carbon dioxide, are separated from the reaction mixture by a gas separator 2. In the first centrifugal separator 3, the resulted slurry is separated into solid and liquid materials. The solid material is conveyed to a slurry drum 4 where the solvent for catalyst recovery is charged. The mixture is then thoroughly stirred and separated in the second centrifugal separator 5. The desired N,N'-disubstituted urea is obtained as a solid after drying in a drier 6. The unreacted materials, solvent, main catalyst, and co-catalyst from the first and second centrifugal separators 3 and 5 are collected in a receiving drum 7. The liquid in the receiving drum 7 is recharged into the reactor 1.

Thus the characteristics of the present invention are to use a sufficient amount of aromatic primary amine which is enough to dissolve catalysts so as to maintain a reaction pressure which is optimal for the reaction and catalyst activity, and use the same aromatic primary amine both as a reactant and as a solvent for catalyst recovery, thereby improving the yield and purity of the desired product remarkably and reusing the catalyst without loss by simple filtration of the product solids.

In the prior art, J. Org. Chem. 40 (19), 2819, 1975, the reaction pressure was only 1 atm., and tri-n-butyl amine was used to minimize the catalyst decomposition since a small amount of aromatic primary amine was employed so that the decomposition of catalyst was not effectively inhibited, and the yield of N,N'-disubstituted urea was as low as about 64%. Furthermore, the catalyst cannot be reused and recycled since the activity of the catalyst was reduced to about 50% of the initial activity, whereas comparing the above disclosure of the present invention, the superiority of the present invention is evident.

The present invention will now be described in more detail in connection with the following examples which should be considered as being exemplary and not limiting the present invention.

In all of these examples, the reaction was carried out by batch mode in an electromagnetic stirring type autoclave made of Hastelloy C having a capacity of 300 ml. Reactants are heated by a heater attached to the outside of the reactor 1. After the reaction was completed, the reaction mixture was cooled down to room temperature by a cooling coil installed at the inside of the reactor 1. The reaction products were analyzed by gas chromatography and high performance liquid chromatography (HPLC). In the gas chromatographic analyses, t-butyl benzene were used as an internal standard.

The yield of N,N'-disubstituted urea calculated by the following equation:

$$\text{Yield (\%)} = \frac{2 \text{ (moles of N,N'-disubstituted urea product)}}{\text{reacted moles of mono-nitro compound and aromatic primary amine}}$$

EXAMPLE 1

Reaction A

Into a 300 ml autoclave were charged 6.15 g (50 mmoles) of nitrobenzene, 27.9 g (300 mmoles) of aniline, 0.15 g of palladium acetate, 1 g of triphenyl phosphine, 2 g of tetraethyl ammonium chloride, t-butyl benzene (as an internal standard for gas chromatographic analysis), and 60 g of xylene. The autoclave was initially purged with carbon monoxide three times, and the carbon monoxide pressure of 40 atm. was established at room temperature. The reaction mixture was heated with stirring and held at 120° C. for 1.5 hours. During the reaction, liquid samples were taken through the sampling valve. After completion of the reaction, the reaction mixture was cooled to room temperature and the gas was discharged from the autoclave. After the filtration of the reaction mixture under the reduced pressure (Supernatant A), the precipitates were washed with 18.6 g (200 mmoles) of aniline (Supernatant B), and 50 g of xylene, and then dried. As a result, 18.4 g of the white precipitate was obtained. Analysis of the remaining solution revealed that the conversion of nitrobenzene was 100% and the yield inductively coupled plasma (ICP) indicated that the palladium component of the catalyst did not present in the product solids. In other words, all the catalyst existed in the filtrate.

Reaction B

Into a 300 ml autoclave were charged the Supernatants A and B obtained from the Reaction A and 6.15 g (50 mmoles) of nitrobenzene. Then the procedure of the Reaction A was repeated. After the filtration of the reaction mixture (Supernatant C), the precipitate was washed with 18.6 g (200 mmoles) of aniline, filtered again (Supernatant D), washed again with 50 g of xylene, and dried. As a result, 18.5 g of white precipitate was obtained. Analysis of the remaining solution revealed that the conversion of nitrobenzene was 100% and the yield of DPU was 98%.

EXAMPLE 2

Into a 300 ml autoclave were charged the Supernatants C and D obtained from the Reaction B of the Example 1 and 6.15 g (50 mmoles) of nitrobenzene. Then the procedure of the Reaction A of the Example 1 was repeated. After the filtration of the reaction mixture (supernatant E), the precipitate was washed with 18.6 g (200 mmoles) of aniline, filtered again (Supernatant F), washed again with 50 g of xylene, and dried. Analysis of the remaining solution revealed that the conversion of nitrobenzene was 100% and the yield of DPU was 98%. The analysis by ICP indicated that the palladium component of the catalyst did not present in the product solids.

EXAMPLE 3

Into a 300 ml autoclave were charged the Supernatants E and F obtained from the Example 2 and 6.15 g (50 mmoles) of nitrobenzene. Then the procedure of the Reaction A of the Example 1 was repeated. As a result, 18.5 g of the white precipitate was obtained. Analysis of the remaining solution revealed that the conversion of nitrobenzene was 100% and the yield of DPU was 98%. The ICP analysis showed that no palladium component present in the product solids.

EXAMPLE 4

The procedure of the Reaction A of the Example A of the Example 1 was repeated except that the xylene was replaced with 60 g of toluene and that the reaction was carried out at 53 atm. and 100° C. for 6 hours. The analysis of the remaining solution revealed that the yield of N,N'-diphenyl urea was 92.4% and the conversion of nitrobenzene was 95.2%.

EXAMPLE 5

Reaction A

The procedure of the Reaction A of the Example 1 was repeated except that tetraethyl ammonium chloride (NEt$_4$Cl) was replaced with tetrabutyl phosphonium bromide (Bu$_4$PBr) and that the reaction was carried out for 4 hours. After the reaction, the product mixture was filtered (Supernatant G), and the precipitate was washed with 18.6 g (200 mmoles) of aniline, filtered again (Supernatant H), washed with xylene (50 g), and dried. Analysis of the remaining solution revealed that the conversion of nitrobenzene was 97.8% and the yield of DPU was 96.4%. The ICP analysis showed that no palladium component present in the product solids.

Reaction B

Into a 300 ml autoclave were charged the Supernatants G and H obtained from the Reaction A of the Example 5 and 6.15 g (50 mmoles) of nitrobenzene. Then the procedure of the Reaction A of the Example 1 was repeated. The conversion of nitrobenzene was 98.4% and yield of DPU was 97.1%.

EXAMPLE 6

Reaction A

The procedure of the Reaction A of Example 1 was repeated except that palladium acetate (Pd(CH$_3$COO)$_2$) was replaced with palladium chloride (PdCl$_2$) and that the reaction was carried out for 6 hours. After the reaction, the product mixture was filtered (Supernatant I), and the precipitate was washed with 18.6 g (200 mmoles) of aniline, filtered again (Supernatant J), washed again with 50 g of xylene, and dried. Analysis of the remaining solution revealed that the conversion of nitrobenzene was 89% and the yield of DPU was 86%. The ICP analysis showed that no palladium component present in the product solids.

Reaction B

Into a 300 ml autoclave were charged the supernatants I and J obtained from the Reaction A of the Example 6 and 6.15 g (50 mmoles) of nitrobenzene. Then the procedure of the Reaction A of the Example 1 was repeated. The conversion of nitrobenzene was 98.4% and the yield of DPU was 97.1%.

EXAMPLE 7

Reaction A

The procedure of the Reaction A of Example 1 was repeated except that palladium acetate (Pd(CH$_3$COO)$_2$) was replaced with palladium trifluoro acetate (Pd(CF$_3$COO)$_2$) and that the reaction was carried out at 62 atm., and 100° C. for 7 hours. After the reaction, the product mixture was filtered (Supernatant K), and the precipitate was washed with 18.6 g (200 mmoles) of aniline, filtered again (Supernatant L), washed with 50 g of xylene, and dried. Analysis of the remaining solution revealed that the conversion of nitrobenzene was 96% and the yield of DPU was 93%. The ICP analysis showed that no palladium component present in the product solids.

Reaction B

Into a 300 ml autoclave were charged the Supernatants K and L obtained from the Reaction A of the Example 7 and 6.15 g of (50 mmoles) of nitrobenzene. Then the procedure of the Reaction A of the Example 1 was repeated. The conversion of nitrobenzene was 97% and the yield of DPU was 94%.

COMPARATIVE EXAMPLE 1

The procedure of the Reaction A of the Example 1 was repeated except that tetraethyl ammonium chloride (NEt$_4$Cl) was omitted. The conversion of nitrobenzene was 11.4% and the yield of DPU was 11.5%.

COMPARATIVE EXAMPLE 2

The procedure of the Reaction A of the Example 1 was repeated except that aniline was omitted. Aniline was not formed and the reaction did not occur.

COMPARATIVE EXAMPLE 3

The procedure of the Reaction A of the Example 1 was repeated except that nitrobenzene was omitted. The reaction did not occur.

COMPARATIVE EXAMPLE 4

The procedure of the Reaction A of the Example 1 was repeated except that tetraethyl ammonium chloride (NEt₄Cl) was replaced with 2 g of potassium chloride (KCl). The yield of N,N'-diphenyl urea was 55.1%, and the conversion of nitrobenzene was 55.5%.

COMPARATIVE EXAMPLE 5

The procedure of the Reaction A of the Example 1 was repeated except that tetraethyl ammonium chloride (NEt₄Cl) was replaced with 2 g of cupric chloride (CuCl₂) and the reaction was carried out at 55 atm. for 5 hours. The reaction did not occur.

COMPARATIVE EXAMPLE 6

The procedure of the Reaction A of the Example 1 was repeated except that palladium acetate (Pd(CH₃COO)₂) was replaced with 1.5 g of palladium metal and the reaction was carried out at 50 atm. and 100° C. for 4.5 hours. The reaction did not occur.

COMPARATIVE EXAMPLE 7

The procedure of the Reaction A of the Example 1 was repeated except that xylene was replaced with 70 ml of acetone. The yield of N,N'-diphenyl urea was 25.1% and the conversion of nitrobenzene was 25.4%.

COMPARATIVE EXAMPLE 8

Reaction A

Into a 300 ml autoclave were charged 6.15 g (50 mmoles) of nitrobenzene, 9.3 g (100 mmoles) of aniline, 0.5 g of palladium acetate, 1 go f triphenyl phosphine, 2 g of tetraethyl ammonium chloride, 5 g of tri-n-butyl amine, t-butyl benzene (as an internal standard for gas chromatographic analysis), and 60 g of xylene. The procedure of the Reaction A of the Example 1 was repeated except that the reaction was carried out at 100° C. for 6 hours. After the reaction, the reaction mixture was filtered under the reduced pressure (Supernatant M), washed with 50 g of xylene, and then dried. Analysis of the remaining solution revealed that the conversion of nitrobenzene was 92% and the yield of DPU was 90%.

Reaction B

Into a 300 ml autoclave were charged the Supernatant M obtained from the Reaction A of the Comparative Example 8, 6.15 g (50 mmoles) of nitrobenzene, and 9.3 g (100 mmoles) of aniline. Then the procedure of the Reaction A of the Comparative Example 8 was repeated. The conversion of nitrobenzene was 28% and the yield of DPU was 26%.

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for preparing N,N'-disubstituted urea of the formula (I)

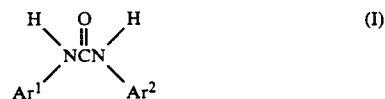

wherein each of $Ar^1$ and $Ar^2$ represents an unsubstituted aromatic radical or an aromatic radical substituted with a halogen atom, a lower alkyl group or a lower alkoxy group, and $Ar^1$ and $Ar^2$ may be similar or different, which comprises reacting an aromatic mono-nitro compound, an aromatic primary amine and carbon monoxide in the presence of a catalyst consisting essentially of a divalent palladium compound as a main catalyst component and ammonium or a phosphonium salt containing halogen atom as a co-catalyst component, and a non-polar solvent, the molar ratio of said aromatic primary amines to said aromatic mono-nitro compound being greater than 2, and the molar ratio of said co-catalyst to said palladium compound being 1 to 20.

2. The process of claim 1, wherein the reaction is constructed at a temperature of 50° to 200° C.

3. The process of claim 1, wherein the reaction is constructed at a pressure of 5 to 100 atm.

4. The process of claim 1, wherein the non-polar solvent is selected from the group consisting of benzene, toluene, and xylene.

5. The process of claim 1, wherein the palladium compound is selected from the group consisting of palladium chloride (PdCl₂), palladium bromide (PdBr₂), palladium iodide (PdI₂), palladium nitrate (Pd(NO₃)₂), palladium sulfate (PdSO₄), palladium acetate (Pd(CH₃COO)₂), palladium trifluoroacetate (Pd(CF₃COO)₂), PdX₂L₂ wherein x represents halogen atom, nitrate, acetate or trifluoroacetate, and L represents PR₃ (R presents methyl, ethyl or butyl), and triphenyl phosphonium radical.

6. The process of claim 1, wherein the halogen atom-containing ammonium salt is selected from the group consisting of tetramethyl ammonium chloride, tetraethyl ammonium chloride, tetrabutyl ammonium chloride, tetramethyl ammonium bromide, tetraethyl ammonium bromide, tetrabutyl ammonium bromide, tetramethyl ammonium iodide, tetraethyl ammonium iodide, and tetrabutyl ammonium iodide.

7. The process of claim 1, wherein the halogen-atom-containing phosphonium salt is selected from the group consisting of tetramethyl phosphonium chloride, tetraethyl phosphonium chloride, tetrabutyl phosphonium chloride, tetramethyl phosphonium bromide, tetraethyl phosphonium bromide, tetrabutyl phosphonium bromide, tetramethyl phosphonium iodide, tetraethyl phosphonium iodide, and tetrabutyl phosphonium iodide.

8. The process of claim 1, wherein the main catalyst, by using an aromatic primary amine in the amount more than 2 moles per mole of mono-nitro compound at the pressure from 5 to 100 atm., is easily recovered by the filtration of the reaction mixture and the washing of the filter cake with said aromatic primary amine.

* * * * *